United States Patent [19]
Steele et al.

[11] Patent Number: 5,767,294
[45] Date of Patent: Jun. 16, 1998

[54] PROCESS FOR THE PRODUCTION OF TRIOXANE FROM FORMALDEHYDE

[75] Inventors: Douglas W. Steele, Bishop; Mahmood N. A. Jawaid, Houston; William Stewart Allen, Kingsville; Norwood E. Thames, Jr.; Dwight A. Reck, both of Corpus Christi, all of Tex.

[73] Assignee: Hoechst Celanese Corporation, Warren, N.J.

[21] Appl. No.: 162,689

[22] Filed: Dec. 6, 1993

Related U.S. Application Data

[63] Continuation-in-part of Ser. No. 18,688, Feb. 17, 1993, abandoned.
[51] Int. Cl.⁶ .................................................. C07D 323/06
[52] U.S. Cl. ................................................... 549/368
[58] Field of Search ...................................... 549/368

[56] References Cited

U.S. PATENT DOCUMENTS

| | | | |
|---|---|---|---|
| 3,378,468 | 4/1968 | Langecker | 203/44 |
| 3,637,751 | 1/1972 | Fuchs | 260/340 |
| 3,697,546 | 10/1972 | Asakawa et al. | 549/368 |
| 3,969,344 | 7/1976 | Ackermann et al. | 260/239.3 |
| 4,043,873 | 8/1977 | Ackermann et al. | 203/46 |
| 4,110,298 | 8/1978 | Wells, III et al. | 260/340 |
| 4,323,502 | 4/1982 | Mück et al. | 260/340 |
| 4,332,644 | 6/1982 | Hamanaka et al. | 203/46 |
| 4,381,397 | 4/1983 | Yoshida et al. | 549/368 |
| 4,493,752 | 1/1985 | Naito et al. | 549/368 |
| 4,504,670 | 3/1985 | Voigt et al. | 549/368 |
| 4,703,129 | 10/1987 | Mück et al. | 549/368 |
| 4,946,561 | 8/1990 | Braun et al. | 203/49 |
| 5,061,349 | 10/1991 | Küppenbender et al. | 203/14 |

FOREIGN PATENT DOCUMENTS 0049250 2/1992 Japan.

*Primary Examiner*—C. Warren Ivy
*Assistant Examiner*—Raymond Covington
*Attorney, Agent, or Firm*—James M. Hunter, Jr.

[57] ABSTRACT

A process for the trimerization of aqueous formaldehyde solution to produce trioxane in a multistage in situ catalyst reactor-extractor column containing a cationic exchange resin. The process entails countercurrent flow of formaldehyde solution and solvent across reactor and extractor stages wherein trioxane, produced from formaldehyde at the reactor stages, is subsequently separated at the extractor stages utilizing a suitable solvent.

20 Claims, 2 Drawing Sheets

PROCESS FOR THE PRODUCTION OF TRIOXANE FROM FORMALDEHYDE

This is a continuation-in-part of copending application Ser. No. 08/018,688 filed on Feb. 17, 1993 now abandoned.

FIELD OF THE INVENTION

The present invention relates to a process for the production of trioxane from aqueous formaldehyde in a multistage in situ catalyst reactor-extractor column.

BACKGROUND OF THE INVENTION

Trioxane may be prepared by the trimerization of an aqueous formaldehyde solution. Generally, the process is conducted in the presence of strong acid and base catalysts and is associated with the production of by-products such as formic acid, methylformate, methylal, trioxepane and tetroxane. Several processes have been developed to convert aqueous formaldehyde solutions into trioxane.

One process, Japanese Patent Laid-Open No. 74524/1992, utilizes a porous membrane containing a reaction catalyst on one surface of the membrane in such a way that a formaldehyde solution is introduced onto the surface of the membrane containing the catalyst while an extractant, incapable of dissolving formaldehyde but capable of dissolving the reaction product, i.e., trioxane, is introduced into another surface of the membrane. A mixture containing a solution of the extractant having the reaction product dissolved therein along with residual formaldehyde is removed from the membrane for separation of formaldehyde from the product in a decanter.

Another process, Japanese Patent Laid-Open No. 49250/1992 utilizes at least two reactors packed with a solid acid or solid base catalyst to prepare trioxane from formaldehyde. Aqueous formaldehyde solution is circulated through the reactors to produce a reaction mixture of trioxane and formaldehyde. The reaction mixture is brought into contact with a solvent in an extraction column operated at 80° C. to separate trioxane from the formaldehyde.

A third process, Japanese Patent Application No. Hei. 04-208,265, suggests the production of trioxane from a concentrated solution of formaldehyde. The formaldehyde solution is circulated through a reactor packed with a solid acid catalyst to produce a reaction product of trioxane and formaldehyde. Thereafter, the reaction product is introduced into an extraction column along with a water-insoluble organic solvent having a boiling point higher than trioxane and free of any azeotropic composition with trioxane, wherein the product is separated into trioxane and solvent by distillation.

Another reference, U.S. Pat. No. 4,703,129, to Muck et al., incorporated herein by reference in its entirety, suggests a process for the continuous preparation of trioxane from an aqueous formaldehyde solution in the presence of an acidic solid-bed catalyst without simultaneous evaporation. According to the disclosure, the reaction is carried out in a reactor containing a bundle of tubes having a preheating zone and the acidic solid-bed catalyst, wherein the catalyst is crosslinked polystyrene containing sulfonic acid groups. Thereafter, the trioxane may be enriched by distillation or extraction.

Although the prior art processes have been adequate for the production of trioxane, they are disadvantaged by the use of multiple units to produce and separate trioxane from formaldehyde. These processes are further disadvantaged by a low "per pass" conversion of formaldehyde to trioxane and subsequent separation of trioxane from aqueous formaldehyde. It is desirable to produce trioxane by way of a process which efficiently utilizes energy and equipment to achieve maximum conversion and separation of trioxane.

SUMMARY OF THE INVENTION

The present invention is directed to a process for the continuous production of trioxane from an aqueous formaldehyde solution in an integrated reactor-extractor column according to the equilibrium reaction:

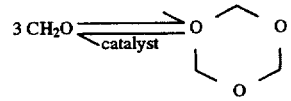

wherein the reaction occurs in an multistage in situ catalyst column with simultaneous reaction and extraction characterized by a column containing a plurality of spaced reactor stages containing a catalyst for reacting an aqueous formaldehyde solution to trioxane, and a plurality of extractor stages for extracting said trioxane into a solvent, said aqueous formaldehyde solution and solvent being in countercurrent flow through the column, said process characterized by the steps of:

(a) charging a solvent that is miscible with trioxane and immiscible with aqueous formaldehyde into the column;

(b) charging an aqueous formaldehyde solution into the column;

(c) reacting the aqueous formaldehyde solution at the reactor stages to trioxane, said trioxane being in reaction equilibrium with formaldehyde in a trioxane-formaldehyde solution;

(d) extracting the trioxane from the trioxaneformaldehyde equilibrium solution into the solvent at the extractor stages to produce a trioxane-rich extract and a trioxane-lean raffinate;

(e) discharging the trioxane-rich extract and trioxane-lean raffinate from the column; and (f) recovering trioxane from the trioxane-rich extract, wherein the extraction of trioxane from the equilibrium solution reduces the concentration of trioxane in the solution wherein the formaldehyde solution reacts at subsequent reactor stages to produce additional trioxane-formaldehyde equilibrium solution.

The process may be conducted in the column without impairment of trioxane extraction or settling, emulsification of the phases, or significant entrainment. The process increases the "one-pass" conversion of trioxane, reduces the recycling of formaldehyde, minimizes the size of the reactor-extractor equipment, as well as conserves energy usage.

BRIEF DESCRIPTION OF THE DRAWINGS

While the specification concludes with claims particularly pointing out and distinctly claiming the present invention, the invention may be better understood from the following description in conjunction with the accompanying drawings in which:

DETAILED DESCRIPTION OF THE INVENTION

Figure 1:
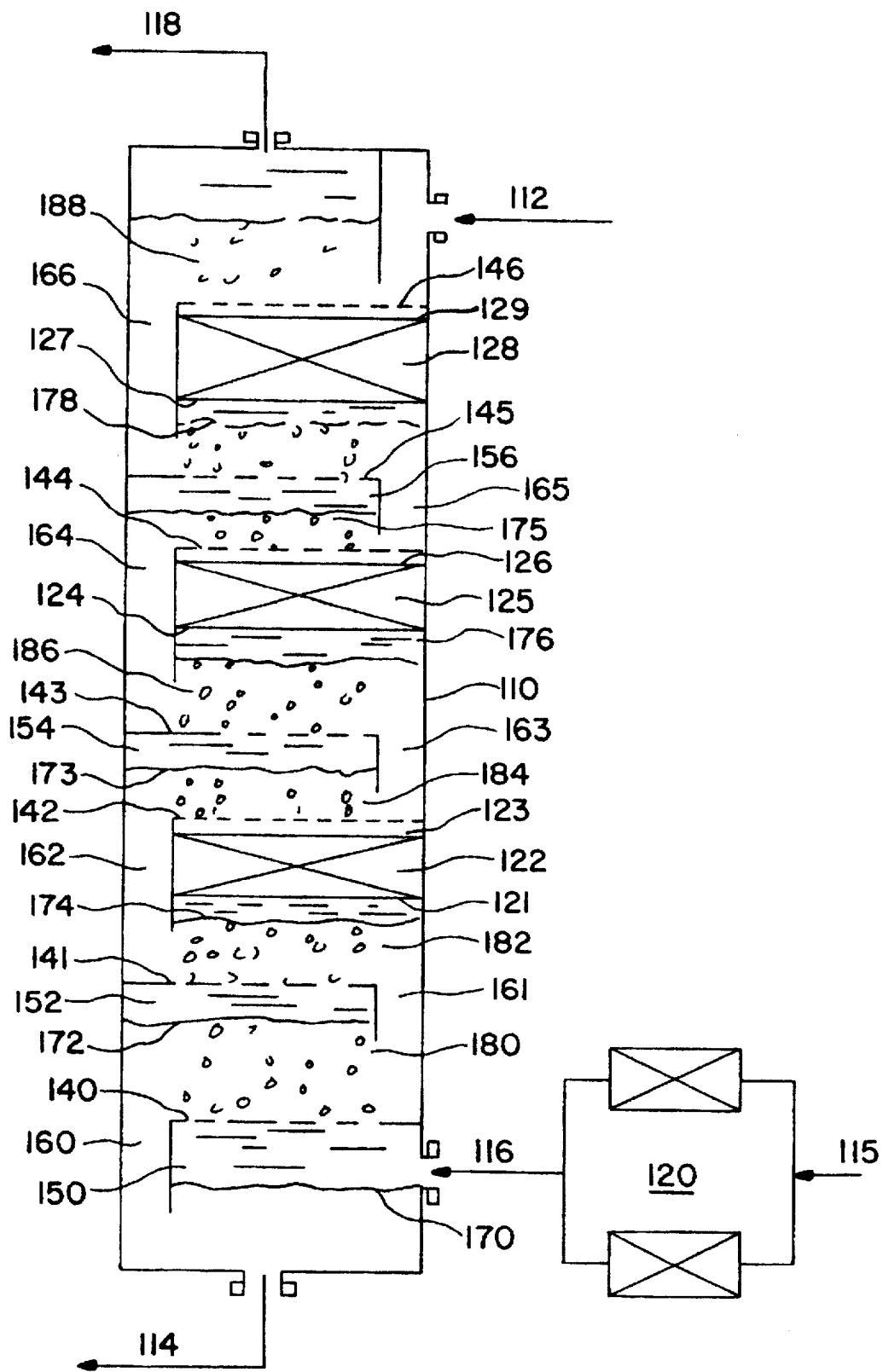
FIG. 1 is a schematic view in elevation of a multistage in situ catalyst reactor-extractor column in which a more dense solvent is charged into the top of the column and a less dense aqueous formaldehyde solution is charged into the bottom of the column.

In accordance with the present invention there is described a process for the continuous production of trioxane from an aqueous formaldehyde solution in a countercurrent flow, multistage in situ catalyst reactor-extractor. The reactor-extractor is characterized as a vertically positioned column having a plurality of horizontally disposed, alternately spaced reactor and extractor stages. An aqueous formaldehyde solution is reacted at the reactor stages into a formaldehyde-trioxane reaction equilibrium solution, and the trioxane is separated from the solution at the extractor stages by countercurrently contacting the solution with a trioxane-miscible solvent. Thereafter, the trioxane is discharged from the column and separated from the solvent by methods known in the art, e.g., distillation, refraction and evaporation.

Trioxane, a trimer of formaldehyde, may be produced from an aqueous formaldehyde solution in the presence of an cationic catalyst according to the equilibrium reaction:

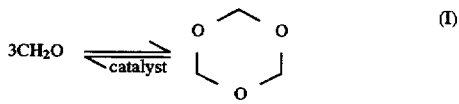

(I)

The equilibrium of the reaction, dependent upon conditions of temperature, pressure, and concentrations of formaldehyde and trioxane in the solution, may be shifted to the right, by removing trioxane from the solution. This process of reducing the concentration of trioxane in the formaldehyde-trioxane equilibrium solution results in an imbalance in the reaction equilibrium of the solution allowing the production of additional trioxane in the presence of the catalyst.

Essentially, the process of the present invention may be characterized by reacting aqueous formaldehyde solution at the reactor stages of the column utilizing a cationic catalyst to produce a trioxane-formaldehyde equilibrium solution, and separating the trioxane from the solution at the extractor stages utilizing a suitable solvent. Removal of trioxane from the equilibrium solution results in an imbalance of reaction equilibrium concentrations of formaldehyde and trioxane in the solution creating the potential of additional trioxane production at subsequent reactor stages. This process of reaction and extraction is repeated at subsequent stages throughout the column until the concentration of formaldehyde in the aqueous solution is so dilute there is no advantage to continuing the process.

One preferred embodiment of the invention relates to a process for the continuous production of trioxane from an aqueous formaldehyde solution according to Formula (I) above, wherein the reaction occurs in a multistage in situ catalyst reactor-extractor characterized as a vertical column having an inlet and outlet positioned at opposing ends of the column for receiving an aqueous formaldehyde solution and discharging a raffinate, and an inlet and outlet positioned at opposing ends of the column for receiving a solvent and discharging an extract, said inlets and outlets being positioned for countercurrent flow, wherein the more dense solvent is charged into the top of the column, and the less dense formaldehyde solution is charged into the bottom of the column; a plurality of vertically spaced reactor stages, each stage containing an inlet for receiving formaldehyde solution from the formaldehyde inlet, a catalyst for reacting formaldehyde solution into trioxane, an outlet for discharging trioxane and formaldehyde, a sieve tray positioned above the outlet and horizontally in the column for receiving trioxane and formaldehyde from the outlet, and a downcomer vertically positioned in the column adjacent to the catalyst and sieve tray; and a plurality of vertically spaced extractor stages for separating trioxane from formaldehyde and discharging formaldehyde to the raffinate outlet, each stage comprising a sieve tray positioned horizontally in the column and a downcomer positioned vertically in the column and adjacent to the sieve tray; said downcomers being positioned for receiving solvent from the solvent inlet and directing said solvent across the sieve trays to the extract outlet, said extractor stages being alternately positioned between the reactor stages, and said downcomer being of sufficient length to provide a formaldehyde-trioxane coalescing zone beneath the reactor and extractor stages and direct the solvent beneath the coalescing zone; said process characterized by the steps of:

(a) charging a solvent that is trioxane-miscible and formaldehyde-immiscible into the column;

(b) charging an aqueous formaldehyde solution into the column;

(c) reacting the aqueous formaldehyde solution at the reactor stages to produce a trioxane-formaldehyde reaction equilibrium solution;

(d) percolating the equilibrium solution through the sieve trays to form droplets;

(e) extracting trioxane from the droplets into the solvent at the extractor stages to produce a trioxane-rich extract and a trioxane-lean raffinate;

(f) discharging trioxane-rich extract and trioxanelean raffinate from the column; and (g) recovering trioxane from the trioxane-rich extract, wherein the extraction of trioxane from the equilibrium solution reduces the concentration of trioxane in the solution and wherein the formaldehyde solution reacts at subsequent reactor stages in accordance with Formula (I) to produce additional trioxane.

The trioxane-rich extract is the solvent containing the trioxane produced at the reactor stages, and the trioxanelean raffinate is the spent formaldehyde solution. The concentration of trioxane in the trioxane-rich extract is greater than that of the trioxane-lean raffinate, and the concentration of formaldehyde in the aqueous formaldehyde solution is greater than that of the trioxane-lean raffinate.

Referring to FIG. 1, there is illustrated a schematic view in elevation of a typical apparatus in which the process of the invention is conducted when the continuous phase is a solvent having a density greater than that of the dispersed phase which is the aqueous formaldehyde solution. Vertically positioned column 110 has attached thereto solvent inlet 112 and extract outlet 114 located at opposite ends of the column for receiving solvent and discharging trioxane-rich extract. Formaldehyde inlet 115 and raffinate outlet 118 are located at opposite ends of the column for receiving aqueous formaldehyde solution and discharging trioxane-lean raffinate so that a continuous, countercurrent flow of dispersed and continuous phases may be maintained in the column. Stream 115 feeds formaldehyde solution to catalytic guard bed reactors 120 which react the solution according to Formula (I) to produce trioxane-formaldehyde reaction equilibrium solution which feeds to the column through inlet 116. Inside the column are located a plurality of horizontally disposed and vertically spaced catalytic bed reactor stages 122, 125 and 128 having inlet sides 121, 124 and 127, and outlet sides 123, 126 and 129. Adjacent to the outlet sides of the reactors are sieve trays 142, 144 and 146. A plurality of horizontally disposed vertically spaced extractor stages 150, 152, 154 and 156 each containing sieve-plate 140, 141, 143, and 145 are positioned above and below the reactor stages. In this arrangement, at least one extractor stage is located between successive reactor stages to provide efficient separation of trioxane from the equilibrium solution. Downcomers 160, 161, 162, 163, 164, 165 and 166 are positioned adjacent to the reactor and extractor stages to direct the flow of solvent from the solvent inlet across the sieve trays to the extract outlet and to provide a zone beneath each extractor and reactor stage for coalescing the aqueous formaldehyde solution. Coalescing zones 170, 172, 173, 174, 175, 176 and 178 are continuous-dispersed phases interfacial areas beneath the reactor and extractor stages. Trioxaneformaldehyde droplets 180, 182, 184, 186, and 188, produced as a result of the dispersed phase passing through the sieve trays, create additional surface area for contacting the solvent and trioxane to provide extraction thereof.

In operation, the continuous phase is charged into solvent inlet 112 to flood the column, and the dispersed phase is charged into formaldehyde inlet 115 at adequate flow rates and reacted at catalytic guard bed reactor 120. An initial reaction according to Formula (I) occurs at the guard bed reactor to produce trioxane in a trioxane-formaldehyde reaction equilibrium solution. The equilibrium solution is fed through inlet 116 into the column. The equilibrium solution accumulates beneath extractor stage 150 to form coalescing zone 170. The height of the coalescing zone increases until the buoyant force is sufficient to overcome the pressure drop across the extractor stage 150. As it flows through extractor stage 150, the dispersed phase percolates through the sieve tray of the extractor stage to form droplets 180. The droplets are contacted with solvent exiting downcomer 161 which extract the trioxane from the equilibrium solution. At extractor stage 152, the extraction operation is repeated by solvent with solvent exiting downcomer 162 to efficiently separate additional trioxane from the solution. As the operation approaches steady state, coalescing zones 170, 172, 173, 174, 175, 176 and 178 are produced beneath successive reactor and extractor stages to overcome the pressure differential created at each stage. The dispersed phase then rises through the sieve trays to form droplets of trioxane-formaldehyde solution 180, 182, 184, 186 and 188. When trioxane is removed from the equilibrium solution by way of extraction, the concentration of trioxane in the solution is reduced. This reduction in trioxane concentration in the reaction solution disturbs the equilibrium of the solution, Formula (I), shifting the equation to the left, i.e., higher concentration of formaldehyde. The reduction of trioxane concentration creates the potential for the production of additional trioxane at subsequent reactor stages. The reduction occurs prior to contact at reactor stage 122 where the trioxane-lean, dispersed phase is reacted to produce additional trioxane, wherein the solution once again approaches reaction equilibrium. The process of reaction followed by extraction is continued throughout the column until the concentration of the formaldehyde solution is reduced by the production and removal of trioxane. The trioxane-rich extract removed from outlet 114 may be processed according to methods known in the art to recover trioxane from the solvent.

Another preferred embodiment of the invention relates to a process for the continuous production of trioxane from an aqueous formaldehyde solution according to Formula (I) above, wherein the reaction occurs in a multistage in situ catalyst reactor-extractor characterized by a vertical column having an inlet and outlet positioned at opposing ends of the column for receiving an aqueous formaldehyde solution and discharging a raffinate, and an inlet and outlet positioned at opposing ends of the column for receiving a solvent and discharging an extract, said inlets and outlets being positioned for countercurrent flow wherein the less dense solvent is charged into the bottom of the column and the more dense formaldehyde solution is charged into the top of the column; a plurality of vertically spaced reactor stages, each stage containing an inlet for receiving formaldehyde solution from the formaldehyde inlet, a catalyst for reacting formaldehyde solution into trioxane, an outlet for discharging trioxane and formaldehyde, a sieve tray positioned above the outlet and horizontally in the column for receiving trioxane and formaldehyde from the outlet, and a downcomer vertically positioned in the column adjacent to the catalyst and sieve tray; a plurality of vertically spaced extractor stages, each stage containing a horizontally disposed sieve tray attached to a vertically disposed downcomer, said downcomer being positioned for receiving solvent from the solvent inlet and directing said solvent beneath the sieve trays to the extract outlet, said downcomers being of sufficient length to provide a trioxaneformaldehyde coalescing zone above the sieve trays and directing the solvent solution above the coalescing zone; said process characterized by the steps of:

(a) charging an aqueous formaldehyde solution into the column;

(b) charging a solvent that is trioxane-miscible and aqueous formaldehyde-immiscible into the column;

(c) reacting the aqueous formaldehyde solution at the reactor stages to produce trioxane wherein the formaldehyde is in equilibrium with the trioxane in a trioxane-formaldehyde solution;

(d) percolating the trioxane-formaldehyde solution through the sieve tray to form droplets;

(e) extracting trioxane from the droplets into the solvent at the extractor stages to produce a trioxane-rich solvent and a trioxane-lean raffinate;

(f) discharging trioxane-rich solvent and trioxanelean raffinate from the column; and (g) recovering trioxane from the trioxane-rich extract, wherein the extraction of trioxane from the trioxaneformaldehyde solution disturbs the balance of the equilibrium equation which provides for the reaction of aqueous formaldehyde solution at subsequent reactor stages to produce additional trioxane.

Figure 2:
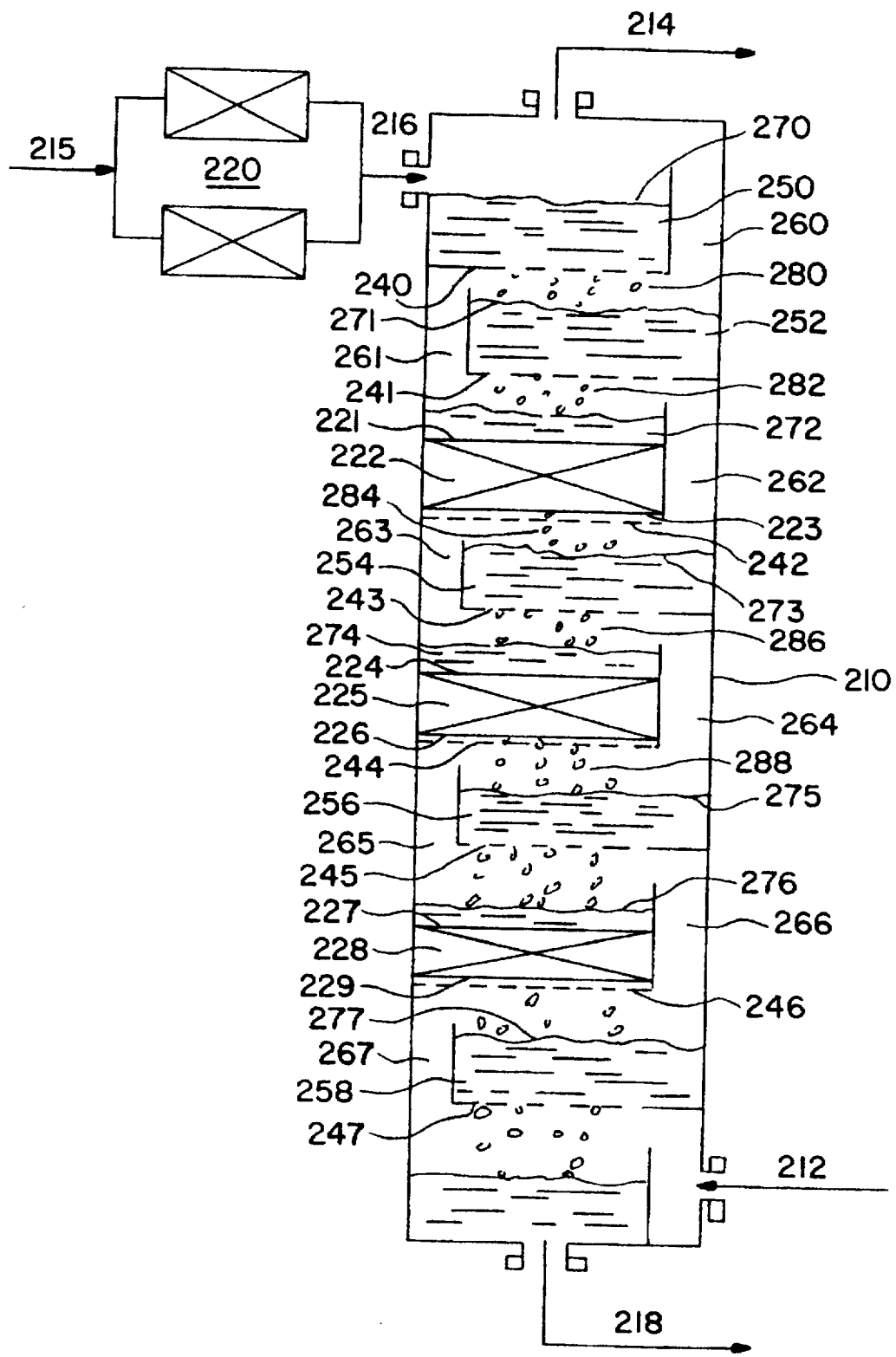
FIG. 2 is a schematic view in elevation of a multistage in situ catalyst reactor-extractor column in which a more dense aqueous formaldehyde solution is charged into the top of the column and a less dense solvent is charged into the bottom of the column.

Referring to FIG. 2, there is illustrated a schematic view in elevation of a typical apparatus in which the multistage in situ catalyst reaction-extraction process is conducted when the aqueous formaldehyde solution has a density greater than that of the solvent. In accordance with this process, the dispersed phase aqueous formaldehyde solution is charged into the top of the column and the continuous phase solvent is charged into the bottom of the column. Vertical column 210 has attached thereto inlet 215 and outlet 218 located at opposite ends of the column for receiving formaldehyde solution and discharging raffinate. Inlet 212 and outlet 214 are located at opposite ends of the column for receiving solvent and discharging extract, so that a continuous, countercurrent flow of formaldehyde solution and solvent is maintained within the column. Stream 215 feeds formaldehyde solution into catalytic guard bed reactor 220 which reacts the solution according to Formula (I) to produce a trioxane-formaldehyde equilibrium solution which feeds to inlet 216. Inside the column are located a plurality of horizontally disposed and vertically spaced catalytic bed reactor stages 222, 225 and 228 each having inlet sides 221, 224 and 227 and outlet sides 223, 226 and 229. Sieve-plates 242, 244 and 246 are located below the outlet sides of the reactor stages, and upcomers 262, 264 and 266 are positioned vertically in the column and located adjacent to the reactor stages and sieve-plates. Alternately spaced between the reactor stages are horizontally disposed extractor stages 250, 252, 254, 256 and 258 each containing a sieve tray 240, 241, 243, 245 and 247 on its lower side. Upcomers 260, 261, 263, 265 and 267 are located adjacent to the extractor stages. The upcomers are positioned to direct the flow of the continuous phase from the solvent inlet to an area beneath the sieve trays and finally to the extract outlet. The upcomers also provide space above each reactor and extractor stage for coalescing of the dispersed phase. Coalescing zones 270, 271, 272, 273, 274, 275, 276 and 277 are located above the extractor and reactor stages. Droplets of dispersed phase 280, 282, 284, 286 and 288 created by the trioxane-formaldehyde solution passing through the sieve trays provide additional surface area for interfacing the continuous and dispersed phases to provide efficient extraction of trioxane into the solvent.

In operation, the continuous phase is charged into solvent inlet 212 to flood the column 210, and, thereafter, the dispersed phase is charged to formaldehyde inlet (215) at adequate flow rates and reacted at catalytic, guard bed reactor 220. An initial reaction according to Formula (I) occurs to produce trioxane in a trioxane-formaldehyde reaction equilibrium solution. The equilibrium solution is fed through inlet 216 into the column. The solution accumulates above extract stage 250 to form coalescing zone 270. The height of the coalescing zone increases until the gravitational force is sufficient to overcome the pressure drop across the extractor stage. Upon overcoming the pressure differential, the dispersed phase percolates down through the sieve tray of the extractor stage to form droplets 280. These droplets contact the continuous phase, wherein trioxane is extracted from the equilibrium solution into the solvent. This process is continued at each stage throughout the column until a steady state operation is achieved to yield a trioxane-rich extract 214 and a trioxane-lean raffinate 218.

The guard bed reactors, i.e., first stage reactors, are typically located outside rather than inside the column to facilitate easy regeneration or replacement of the catalyst. Due to metallic cation contaminates, e.g., potassium, sodium, etc., in the aqueous formaldehyde solution, it is convenient to place the initial reactor stage outside the column to prevent column contamination. However, if desired, the initial reactor may be located inside the column.

The solvent may be recycled after separation of the trioxane produced therefrom, and the trioxane-lean raffinate (i.e., spent, aqueous formaldehyde solution) may be reconcentrated for recycling to the process.

The column is generally fabricated from a metallic or other suitable material and may contain an inert liner. It is of sufficient height and diameter to accommodate a plurality of extractor and reactor stages to maintain a relatively high conversion and extraction of trioxane. The sieve trays may contain multiple holes, typically in the range of about 0.01 to about 0.5 inches, and preferably in the range of from about 0.03 to about 0.3 inches in diameter. The holes are typically spaced from about 0.5 to about 0.75 inches apart. The sieve trays function to create additional surface area of the dispersed phase to provide efficient extraction.

Typically, the extractor and reactor stages are alternately spaced in the column to achieve efficient reaction and extraction of trioxane. However, this arrangement may be replaced with the preferred sequence of one reactor stage followed by two extractor stages. Based on the miscibility of trioxane with the solvent, this arrangement generally provides efficient removal of the trioxane from the equilibrium solution. Other sequences embodying the arrangement of extractor and reactor stages in accordance with the invention will become apparent to those skilled in the art.

The trimerization of aqueous formaldehyde solution generally occurs in the presence of a solid acidic catalyst. Typically, the catalyst is a macroreticular or macroporous cation exchange resin having sulfonic acid groups. Suitable acid groups may be provided by sulfuric acid, methanesulfonic acid, p-toluenesulfonic acid, etc. Convenient catalyst carriers may be selected from zeolites, i.e., silica alumina, alumina, silicon carbide, solids based on water-containing metal oxides such as iron (III) oxide, zirconium dioxide, titanium dioxide, and mixtures thereof. These carriers may be impregnated with the sulfonic acid groups and calcinated at relatively high temperatures to provide a suitable catalyst. Solid acid catalyst made from crosslinked polytetrafluoroethylene or styrene divinylbnezene copolymers containing active sulfonic groups are suitable catalyst for the process, e.g., sulfonated polystyrene divinylbenzene copolymer, perfluoronated polymer sulfonic acid, and perfluorosulfonate polymer. A particularly preferred catalyst is Amberiyst™ XN-1010 distributed by Rohm and Haas Company, Philadelphia, Pa. This catalyst is a sulfonated, crosslinked, styrenedivinylbenzene copolymer in the hydrogen form. It is typically characterized by a particle size of about 16 to about 50 mesh, e.g., preferably greater than about 30 mesh, a mean pore diameter of about 50 Å, a porosity of about 41 percent, a surface area of about 450 $m^2/gm$, a cation exchange capacity of about 3.1 meq/gm, and a bulk density of about 33 $lbs/ft^3$. The void volume of the catalytic bed within each reactor stage is generally in the range of about 10 to about 90 percent, and preferably in the range of about 20 to about 60 percent. The pressure drop across the bed is typically in the range of about 0.25 to about 12 inches of reaction phase. It is preferable to keep the pressure drop in the range of about 1 to about 6 inches of reaction phase. The beds will typically contain from about 1 to about 12 inches in height of the catalyst which may be packed between plastic or metallic screens.

Suitable solvents for the process may be selected using the empirical equation:

$$DC=0.025A+0.05B+0.0087C+0.016D+0.22$$

wherein DC is the distribution coefficient, A is the mole percent of ether functional group in the solvent molecule, B is the mole percent of ketone functional group in the solvent molecule, C is the mole percent of phenyl functional group in the solvent molecule, and D is the mole percent of chlorine on aliphatic carbons in the solvent molecule. Generally, solvents exhibiting a DC of at least about 0.75 are suitable for the process. The distribution coefficient may be defined as the weight of the component in one pound of the organic phase divided by the weight in one pound of the aqueous phase. The method of determining suitable solvents and coefficients are listed in Example 7 and Table I, respectively.

While many liquid solvent that are immiscible with formaldehyde and miscible with trioxane may serve as a suitable extraction component for the process, suitable solvents will generally exhibit a density greater or less than that of the aqueous formaldehyde solution to promote gravitational flow, and may be selected from saturated or unsaturated lower aliphatic hydrocarbons or halosubstituted derivatives thereof. Solvents that tend to work well with the invention are ketones, ethers, as well as those containing aromatic functional groups and halogenated derivatives thereof. Typically, the solvent is selected from hexane, cyclohexane, pentane, heptane, ethylbenzene, monochlorobenzene, orthodichlorobenzene, paradichlorobenzene, benzophenone, acetophenone, anisole, trimethylbenzene, tetramethylbenzene, toluene, o-, m-, and p-xylenes, biphenyl, diphenyl ether, and methylene chloride.

The density of the solvent (relative to the density of water) will generally determine whether the flow of the aqueous formaldehyde solution in the column will be in the direction of or against gravity. Solvents exhibiting a density greater than that of aqueous formaldehyde solution may be selected from orthodichlorobenzene, methylene chloride, diphenyl ether, monochlorobenzene, paradichlorobenzene, acetophenone, benzophenone, and mixtures thereof. Solvents exhibiting a density less than that of aqueous formaldehyde solution may be selected from anisole, benzene, hexane, cyclohexane, pentane, ethylbenzene, trimethylbenzene, tetramethylbenzene, toluene, o-, m-, and p-xylene, and mixtures thereof.

Generally, the aqueous formaldehyde solution should contain at least about 35 percent by weight of formaldehyde. Typically, the solution should contain from about 50 to about 80 percent by weight, and preferably from about 60 to about 70 percent by weight of formaldehyde. The aqueous formaldehyde solution utilized in the process of the present invention is typically concentrated by evaporation, distillation or other methods known to those skilled in the art. Spent formaldehyde solution may be combined with feedstock solution prior to concentration and recycled into the process. The aqueous formaldehyde solution is typically filtered to remove any foreign matter prior to being charged into the guard bed reactors and column.

The dispersed phase, typically, may be charged into the column at a flow rate in the range of from about 0.1 to about 10 ml/cm$^2$/min, and preferably in the range of from about 1 to about 4 ml/cm$^2$/min. The volume ratio of the continuous phase to dispersed phase may be in the range of about 0.5 to 20, and preferably in the range of about 3 to 10.

The following examples are general illustrations of the process of preparing trioxane according to the present invention. They are provided for purposes of exemplification only as should be appreciated from the foregoing discussion. Other arrangements of the reactor and extractor stages within the scope of the invention will readily become apparent to those skilled in the art.

EXAMPLE 1

Utilizing an apparatus similar to that of FIG. 1, the guard bed reactor contained a +30 mesh Amberlyst XN1010 cationic exchange resin. The column was 2" dia.×102" ht. and contained two (2) catalytic bed reactor stages and six (6) extractor stages. The catalytic beds were 12" ht. each containing about 240 gms of +30 mesh Amberlyst XN1010. The resin was placed in screens to reduce the pressure drop across the reactor bed. Twenty (20) percent of the bed space was reserved for catalyst expansion and to assist in pressure drop reduction. The empty space, however, is filled due to resin expansion during the flow of formaldehyde solution and solvent through the column. The sieve trays contained four sets of 0.055" holes on the corners of 1"×0.6" rectangulars. The downcomers, made of plastic measured ⅛" in diameter. The length of the downcomers were about 5.5" with the exception that the length of the downcomers at the reactor beds were about 19.5" in length. The outlet side of the catalytic beds were about 0.25" from sieve trays above them, and inlet side of the beds were about 18" from sieve trays beneath them. The distance between two adjacent extractor stages was about 6".

A 51% by weight aqueous formaldehyde solution, containing 0.56% by weight of trioxane, was charged through the guard bed at a rate of 59 gm/min to produce an equilibrium solution containing 1.81% by weight of trioxane. The solvent, containing 0.31% by weight of trioxane, was fed countercurrent to the formaldehyde solution at a flow rate of 426 gm/min (solvent-to-formaldehyde weight ratio of 7.2). The concentration of trioxane in the extract and raffinate were 0.71% and 0.63% by weight, respectively. The trioxane production rate in the solvent was 1.70 gm/min compared to about 0.74 gm/min by conventional processes. The temperature of the column during operation was maintained between 95° and 100° C. The percent conversion of trioxane in the solvent was calculated to be 5.7% by weight. There was a 60% increase in trioxane conversion/production rate over conventional processes.

EXAMPLE 2

Utilizing a column of Example 1, an aqueous formaldehyde solution containing 52% by weight of formaldehyde was charged through the guard bed reactor to produce a trioxane-formaldehyde equilibrium solution containing 1.78% by weight of trioxane. The equilibrium solution was fed to the column at a rate of 68 gm/min. The solvent, containing 0.68% by weight of trioxane, was fed countercurrent to the formaldehyde at a flow rate of 436 gm/min (solvent-to-formaldehyde weight ratio of 6.4). The concentrations of trioxane in the solvent and raffinate were 1.00% and 1.01% by weight, respectively. The trioxane production rate in the solvent was 1.40 gm/min compared to 1.21 gm/min utilizing conventional processes. The temperature of the column was maintained within the range of 95° and 100° C. The conversion rate of trioxane in the solvent phase was 4.0% by weight. There was a 16% increase in trioxane conversion/production rate over conventional processes.

EXAMPLE 3

Utilizing the column of Example 1, an aqueous formaldehyde solution containing 73.3% by weight of formaldehyde and 0.02% by weight of trioxane was charged through the guard bed reactor to produce an equilibrium solution containing 4.9% by weight of trioxane. The solution was subsequently charged to the column at a flow rate of 66 gm/min. The solvent, containing 1.32% by weight of trioxane, was fed countercurrent to the formaldehyde solution at a rate of 465 gm/min (solvent-to-formaldehyde weight ratio of 7.0). The concentration of trioxane in the extract and raffinate were 2.43 and 1.64 percent by weight, respectively. The trioxane production rate in the solvent was 5.16 gm/min compared to 3.22 gm/min utilizing conventional processes. The temperature of the column was maintained within the range of 95° and 100° C. The conversion rate of trioxane was 10.7%. There was a 60% increase in trioxane conversion/production rate over conventional processes.

EXAMPLE 4

An aqueous formaldehyde solution containing 63% by weight of formaldehyde was charged through the guard bed reactor to produce an equilibrium solution containing 3.7% by weight of trioxane. The equilibrium solution was charged into a column similar to that of Example 1 with the except that the column contained 18 reactor stages and 57 extractor stages. Three extractor stages were placed between each reactor stage, and two extractors were placed above the dispersed phase inlet. The distance between adjacent extractor stages was 6", while the distance between the outlet side of the catalytic bed and the sieve tray above it was 6". The distance between the sieve tray and catalytic bed inlet was 12". The equilibrium solution was charged into the column at a rate of 65 gm/min. The solvent, containing 0% of trioxane, was fed to the column at a flow rate of 208 gm/min (solvent-to-formaldehyde weight ratio of 3.2). The concentration of trioxane in the extract and raffinate were 2.2 and 0.3% by weight, respectively. The trioxane production rate in the solvent was 4.58 gm/min compared to 2.41 gm/min utilizing conventional processes. The temperature of the column was maintained within the range of 95° and 100° C. The conversion rate of trioxane was 11.2%. There was a 90% increase in trioxane conversion/production rate over conventional processes.

EXAMPLE 5

An aqueous formaldehyde solution containing 64% by weight of formaldehyde was charged through the guard bed reactor to produce an equilibrium solution containing 3.6% by weight of trioxane. The solution was charged into a column similar to that of Example 4 at a rate of 65 gm/min. The solvent, containing 0% of trioxane, was fed to the column at a flow rate of 195 gm/min (solvent-to-formaldehyde weight ratio of 3.0). The concentration of trioxane in the extract and raffinate were 2.4 and 0.4% by weight, respectively. The trioxane production rate was 4.68 gm/min compared to 2.34 gm/min utilizing conventional processes. The temperature in the column was maintained within the range of 95° and 100° C. The conversion rate of trioxane in the solvent phase was 11.3%. There was a 100% increase in trioxane conversion/production rate over conventional processes.

EXAMPLE 6

An aqueous formaldehyde solution containing 59% by weight of formaldehyde was charged through the guard bed reactor to produce an equilibrium solution containing 2.6% by weight of trioxane. The solution was charged into a column similar to that of Example 4 at a rate of 65 gm/min. The solvent, containing 1.2% by weight of trioxane, was fed to the column at a flow rate of 338 gm/min (solvent-to-formaldehyde weight ratio of 5.2). The concentration of trioxane in the extract and raffinate were 2.6% and 0% by weight, respectively. The trioxane production rate was 4.73 gm/min compared to 1.69 gm/min utilizing conventional processes. The temperature in the column was maintained within the range of 95° and 100° C. The conversion rate of trioxane was 12.3%. There was a 180% increase in trioxane conversion/production rate over conventional processes.

EXAMPLE 7

To determine the Distribution Coefficient, DC, of solvents suitable for the process of the invention, a stock solution of trioxane, formaldehyde and water was prepared from paraform and pure trioxane. The exact formaldehyde concentration was determined by sulfite titration, and the trioxane concentration was calculated from the weights of water and trioxane added to the stock. Approximately 8 gms of the stock solution were weighed (accurate to ±0.01 gm) into ~20 ml septum ("headspace") vial, approximately 8 gms of the solvent were weighed into the septum vial, and the vial was sealed using a Teflon® septum. The vial was placed in a basket in a mineral oil bath and heated with a Haale heater-circulator capable of maintaining the required temperature of 25°, 60° or 90° C. (±0.5° C.). After temperature equilibration, the vial was removed from the oil, shaken vigorously for ~20 seconds, and quickly returned to the bath (this sequence was repeated at least 3 times for each solvent). Following the final shaking, the solvent and aqueous layers were allowed to separate completely. A minute amount of the organic phase was then withdrawn form the vial using a 1 microliter gas chromatograph ("GC") syringe. The organic phase was then analyzed by GC using the following conditions:

Instrument: Varian 1700

Detector: TC

Detector Temp: 175° C.

Injector Temp: 175° C.

Column Temp: 95° C.

Program: Isothermal

Detector Current: 275 mA

Attenuation: 8

Carrier Gas: He, ~30 ml/min

Sample size: 0.5 µl

Column: 6'×⅛" SS, Celcon® M-25 Drier Product, 100–120 mesh

Calibration: Trioxane and HCHO by external standard (the "stock") soln. calibrated using a saturated soln. of methyl isobutyl ketone (1.9% $H_2O$)

Trioxane DCs were determined using this experimental procedure for a number of solvents. An equation was developed to allow prediction of untested solvents based on functional group composition of the molecule. Table I lists the functional group composition of a number of potential solvents, the equation for predicting the DC, and a comparison of predicted and experimental DCs for these solvents.

TABLE I

| | Mole % of Functional Group | | | | | |
|---|---|---|---|---|---|---|
| Solvent | Ether (—O—) | Ketone (C=O) | Phenyl ($C_6H_5$) | Chlorine on Aliphatic Carbons | DC Predicted | DC Experimental |
| Benzyl Ether | 8 | | 78 | | 1.10 | 0.98 |
| Cyclohexanone | | 28 | | | 1.67 | 1.64 |
| Isopentyl Ether | 10 | | | | 0.47 | 0.47 |
| Phenyl Cyclohexane | | | 48 | | 0.64 | 0.71 |

TABLE I-continued

| Solvent | Ether (—O—) | Ketone (C=O) | Phenyl (C₆H₅) | Chlorine on Aliphatic Carbons | DC Predicted | DC Experimental |
|---|---|---|---|---|---|---|
| 2-Methyl Cyclohexanone | | 25 | | | 1.47 | 1.49 |
| 2-Heptanone | | 25 | | | 1.47 | 1.59 |
| p-xylene | | | 71 | | 0.84 | 1.05 |
| i-Butyl Heptyl Ketone | | 15 | | | 0.97 | 0.84 |
| Mineral Oil | | | | | 0.22 | 0.13 |
| Cyclooctanone | | 22 | | | 1.67 | 1.77 |
| 2,2-Dichloroethyl ether* | 11 | | | 50 | 1.30 | 1.70 |
| Acetophenone* | | 23 | 64 | | 1.93 | 1.69 |
| o-xylene | | | 71 | | 0.84 | 0.90 |
| Benzophenone* | | 15 | 85 | | 1.71 | 1.70 |
| Tetralin | | | 58 | | 0.72 | 0.62 |
| Cumene | | | 64 | | 0.78 | 0.65 |
| Phenyl Ether* | 11 | | 89 | | 1.27 | 1.71 |
| D: N-Butyl Ether | 12 | | | | 0.53 | 0.62 |
| Anisole | 15 | | 71 | | 1.21 | 1.21 |
| 1,2,4-Trimethyl Benzene | | | 63 | | 0.77 | 0.50 |
| Butyl Phenyl Ether | 11 | | 51 | | 0.66 | 0.81 |
| Biphenyl* | | | 100 | | 1.09 | 1.06 |

*Indicates that the potential for significant interactions between functional groups exists in these molecules.

We claim:

1. A process for the continuous production of trioxane from an aqueous formaldehyde solution in an integrated reactor-extractor column according to the equilibrium reaction:

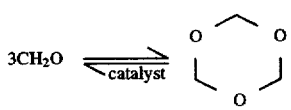 (I)

wherein the reaction occurs in an multistage in situ catalyst column with simultaneous reaction and extraction comprising a column consisting essentially of a plurality of reactor stages comprising a catalyst for reacting an aqueous formaldehyde solution to trioxane, and a plurality of extractor stages for extracting trioxane into a solvent, said formaldehyde solution and solvent being in wherein the more dense solution or solvent is charged into the top of the column and the less dense solution solvent or solution is charged into the bottom of the column, said process comprising the steps of:

(a) charging a solvent that is miscible with trioxane and immiscible with aqueous formaldehyde into the column;

(b) charging an aqueous formaldehyde solution into the column;

(c) reacting the aqueous formaldehyde solution at the reactor stages to produce trioxane, said trioxane being in reaction equilibrium with formaldehyde in a trioxane-formaldehyde equilibrium solution;

(d) extracting the trioxane from the trioxaneformaldehyde solution into the solvent at the extractor stages to produce a trioxane-rich extract and a trioxane-lean raffinate;

(e) discharging the trioxane-rich extract and trioxane-lean raffinate from the column; and (f) recovering trioxane from the trioxane-rich extract; wherein the extraction of trioxane from the equilibrium solution reduces the concentration of trioxane in the solution wherein the formaldehyde solution reacts at subsequent reactor stages to produce additional trioxane-formaldehyde equilibrium solution.

2. The process according to claim 1, wherein the aqueous formaldehyde solution charged into the column is at least about 35 weight percent formaldehyde.

3. The process according to claim 2, wherein the catalyst is a cationic exchange resin comprising a sulfonated crosslinked styrene-divinylbenzene copolymer in the hydrogen form.

4. The process according to claim 3, wherein the solvent is selected from the group consisting of hexane, cyclohexane, pentane, heptane, ethylbenzene, biphenyl, monochlorobenzene, orthodichlorobenzene, paradichlorobenzene, benzophenone, acetophenone, anisole, trimethylbenzene, tetramethylbenzene, toluene, o-, m-, and p-xylenes, diphenyl ether, methylene chloride, and mixtures thereof.

5. A process for the continuous production of trioxane from an aqueous formaldehyde solution according to the equilibrium reaction:

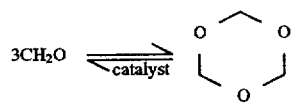 (I)

wherein the reaction occurs in a multistage in situ catalyst reactor-extractor comprises a vertical column having an inlet and outlet positioned at opposing ends of the column for receiving an aqueous formaldehyde solution and discharging a raffinate, and an inlet and outlet positioned at opposing ends of the column for receiving a solvent and discharging an extract, said inlets and outlets being positioned for countercurrent flow, wherein the more dense solvent is charged into the top of the column, and the less dense formaldehyde solution is charged into the bottom of the column; a plurality of vertically spaced reactor stages, each stage comprising an inlet for receiving formaldehyde solution from the formaldehyde inlet, a catalyst for reacting formaldehyde solution into trioxane, an outlet for discharging trioxane and formaldehyde, a sieve tray positioned above the outlet and horizontally in the column for receiving trioxane and formaldehyde from the outlet, and a downcomer vertically positioned in the column adjacent to the catalyst and sieve tray; and a plurality of vertically spaced extractor stages for separating trioxane from formaldehyde, each stage comprising a sieve tray positioned horizontally in the column and a downcomer positioned vertically in the column and adjacent to the sieve tray; said downcomers being positioned for receiving solvent from the solvent inlet and directing said solvent across the sieve trays to the extract outlet, said extractor stages being alternately positioned between the reactor stages, and said downcomer being of sufficient length to provide a formaldehyde-trioxane coalescing zone beneath the reactor and extractor stages and direct the solvent beneath the coalescing zone; said process comprising the steps of:

(a) charging a solvent that is trioxane-miscible and formaldehyde-immiscible into the column;

(b) charging an aqueous formaldehyde solution into the column.

(c) reacting the aqueous formaldehyde solution at the reactor stages to produce a trioxane-formaldehyde reaction equilibrium solution;

(d) percolating the equilibrium solution through the sieve trays to form droplets;

(e) extracting trioxane from the droplets into the solvent at the extractor stages to produce a trioxane-rich extract and a trioxane-lean raffinate;

(f) discharging trioxane-rich extract and trioxane-lean raffinate from the column; and (g) recovering trioxane from the trioxane-rich extract, wherein the extraction of trioxane from the reaction equilibrium solution reduces the concentration of trioxane in the solution and wherein the formaldehyde solution reacts at subsequent reactor stages in accordance with Formula (I) to produce additional trioxane.

6. The process according to claim 5, wherein the solvent is selected from the group consisting of orthodichlorobenzene, methylene chloride, diphenyl ether, monochlorobenzene, paradichlorobenzene, acetophenone, benzophenone, and mixtures thereof.

7. The process according to claim 6, wherein the solvent is orthodichlorobenzene.

8. The process according to claim 7, wherein the catalyst is a cationic exchange resin comprising a sulfonated, crosslinked, styrene-divinylbenzene copolymer in the hydrogen form.

9. The process according to claim 8, wherein the aqueous formaldehyde solution contains from about 35 to about 85 weight percent of formaldehyde.

10. The process according to claim 9, wherein the initial reactor is a guard bed reactor located outside the column.

11. The process according to claim 10, wherein the column is operated at a temperature of at least about 95° C.

12. A process for the continuous production of trioxane from an aqueous formaldehyde solution according to the equilibrium reaction:

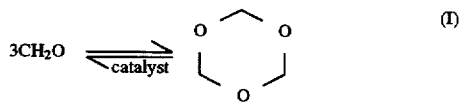

wherein the reaction occurs in a multistage in situ catalyst reactor-extractor comprising by a vertical column having an inlet and outlet positioned at opposing ends of the column for receiving an aqueous formaldehyde solution and discharging a raffinate, and an inlet and outlet positioned at opposing ends of the column for receiving a solvent and discharging an extract, said inlets and outlets being positioned for countercurrent flow wherein the less dense solvent is charged into the bottom of the column, and the more dense formaldehyde solution is charged into the top of the column; a plurality of vertically spaced reactor stages, each stage containing an inlet for receiving formaldehyde solution from the formaldehyde inlet, a catalyst for reacting formaldehyde solution into trioxane, an outlet for discharging trioxane and formaldehyde, a sieve tray positioned above the outlet and horizontally in the column for receiving trioxane and formaldehyde from the outlet, and a downcomer vertically positioned in the column adjacent to the catalyst and sieve tray; a plurality of vertically spaced extractor stages, each stage comprising a horizontally disposed sieve tray attached to a vertically disposed downcomer, said downcomer being positioned for receiving solvent from the solvent inlet and directing said solvent beneath the sieve trays to the extract outlet, said downcomers being of sufficient length to provide a trioxaneformaldehyde, coalescing zone above the sieve trays and directing the solvent solution above the coalescing zone; said process comprising the steps of:

(a) charging an aqueous formaldehyde solution into the column, (b) charging a solvent that is trioxane-miscible and aqueous formaldehyde-immiscible into the column;

(c) reacting the aqueous formaldehyde solution at the reactor stages to produce trioxane wherein the formaldehyde is in equilibrium with the trioxane in a trioxane-formaldehyde solution;

(d) percolating the trioxane-formaldehyde solution through the sieve tray to form droplets;

(e) extracting trioxane from the droplets into the solvent at the extractor stages to produce a trioxane-rich solvent and a trioxane-lean raffinate;

(f) discharging trioxane-rich solvent and trioxane-lean raffinate from the column; and (g) recovering trioxane from the trioxane-rich extract, wherein the extraction of trioxane from the trioxaneformaldehyde solution disturbs the balance of the reaction equilibrium which provides for the reaction of aqueous formaldehyde solution at subsequent reactor stages to produce additional trioxane.

13. The process according to claim 12, wherein the solvent is selected from the group consisting of anisole, benzene, biphenyl, hexane, cyclohexane, pentane, ethylbenzene, trimethylbenzene, tetramethylbenzene, toluene, o-, m-, and p-xylene, and mixtures thereof.

14. The process according to claim 13, wherein the solvent is biphenyl.

15. The process according to claim 14, wherein the catalyst is sulfonated cationic exchange resin.

16. The process according to claim 15, wherein the aqueous formaldehyde solution contains at least about 35 percent by weight of formaldehyde.

17. The process according to claim 16, wherein the initial reactor is a guard bed reactor.

18. The process according to claim 12, wherein the column is operated at a temperature of at least about 95° C.

19. The process according to any one of claims 1–3, 5, 8–12 and 15–18, wherein the solvent is selected from the group exhibiting a distribution coefficient (DC) greater than 0.75 according to the equation:

$DC=0.025A+0.05B+0.0087C+0.016D+0.22$ wherein A is the mole percent of ether functional group in the solvent molecule, B is the mole percent of ketone functional group in the solvent molecule, C is the mole percent of phenyl functional group in the solvent molecule, and D is the mole percent of aliphatic carbons in the solvent molecule.

20. An apparatus for the continuous production of trioxane from an aqueous formaldehyde solution according to the equilibrium reaction:

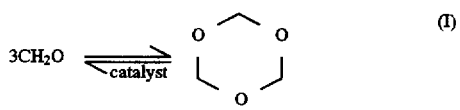

wherein said reaction occurs in a multistage in situ catalyst reactor-extractor comprising a vertically positioned column having an inlet and outlet positioned at opposing ends of the column for receiving an aqueous formaldehyde solution and discharging a raffinate, and an inlet and outlet positioned at opposing ends of the column for receiving a solvent solution and discharging an extract, said inlets and outlets being positioned for countercurrent flow wherein the more dense, solution is charged into the top of the column, and the less dense, solution is charged into the bottom of the column; a plurality of horizontally position reactor stages, each stage comprising a catalyst, a sieve tray, an inlet for receiving formaldehyde solution from the formaldehyde inlet, and an outlet for discharging a trioxane-formaldehyde solution to the sieve tray; and a plurality of horizontally positioned extractor stages, each stage comprising a sieve tray for extracting trioxane from the trioxane-formaldehyde solution into a solvent, wherein said reactors and extractors being alternately spaced in said column.

* * * * *